US00PP19036P2

(12) United States Plant Patent
Lim

(10) Patent No.: US PP19,036 P2
(45) Date of Patent: Jul. 15, 2008

(54) SHRUB PLANT NAMED 'BAIRIFT'

(50) Latin Name: *Rosa hybrida*
Varietal Denomination: BAIrefit

(75) Inventor: Peter P. Lim, McMinnville, OR (US)

(73) Assignee: Bailey Nurseries Inc., Newport, MN (US)

( * ) Notice: Subject to any disclaimer, the term of this patent is extended or adjusted under 35 U.S.C. 154(b) by 0 days.

(21) Appl. No.: 11/809,230

(22) Filed: May 31, 2007

(51) Int. Cl.
*A01H 5/00* (2006.01)

(52) U.S. Cl. ..... Plt./103

(58) Field of Classification Search ..... Plt./103
See application file for complete search history.

*Primary Examiner*—Kent L Bell
(74) *Attorney, Agent, or Firm*—Penny J. Aguirre

(57) ABSTRACT

A new cultivar of shrub rose, *Rosa* 'BAIrift', characterized by its flowers that are very full, colored white with an apricot center, and fragrant flowers, its uniformly upright and arching plant habit and its recurrent blooming habit. The new variety has medium green glossy foliage that is resistant to black spot and powdery mildew, is readily propagated on its own roots and is hardy in U.S.D.A. Zones 4 to 9.

2 Drawing Sheets

Botanical classification: *Rosa hybrida.*
Variety denomination: 'BAIrift'.

BACKGROUND OF THE INVENTION

The present invention relates to a new and distinct cultivar of *Rosa hybrida.* The new cultivar will be referred to hereafter by its cultivar name, 'BAIrift'. 'BAIrift' is a shrub rose suitable for landscape plantings.

The new cultivar of shrub rose is a selection from a controlled breeding program conducted by the inventor in Yamhill, Oreg. with a focus to create cultivars of roses with greater winter hardiness and improvements in disease resistance combined with good flower quality.

The new variety of shrub rose, 'BAIrift', designated as seedling No 99A796 was selected among seedlings derived from a cross made in Yamhill, Oreg. in 1999 between the female parent, 'MACrexy' (U.S. Plant No. 6,713) and the male parent, 'MEIpotal' (U.S. Plant Pat. No. 8,841) as the male parent. 'BAIrift' was selected as unique and budded onto understock in August 2000 and reselected by the inventors for its distinct characteristics in 2005.

The new cultivar has been asexually propagated by rooting of softwood cuttings from a plant grown on its own roots in Yamhill, Oreg. Asexual propagation determined that the characteristics of this cultivar are stable and are reproduced true to type in successive generations.

SUMMARY OF THE INVENTION

The following traits have been repeatedly observed and represent the characteristics of the new rose as observed for a period of three years in Yamhill, Oreg. and further evaluated at several other test sites in the U.S. These attributes in combination distinguish 'BAIrift' as a unique cultivar of shrub rose.

1. 'BAIrift' exhibits very fully creamy white colored flowers with apricot colored centers with color retention until flower drop. Classified as white by American Rose Society standards.

2. 'BAIrift' exhibits a uniform, upright and arching plant habit with blooms covering the plant throughout the plant.
3. 'BAIrift' exhibits medium green foliage.
4. 'BAIrift' is a recurrent bloomer.
5. 'BAIrift' has shown excellent resistance to rose blackspot (*Diplocarpon rosae*) and powdery mildew (*Sphaerotheca pannosa* var. *rosa*).
6. 'BAIrift' is very fragrant.
7. 'BAIrift' is hardy in U.S.D.A. Zones 4 to 9.
8. 'BAIrift' is a vigorous grower and readily propagated by softwood cuttings and grown on its own roots.

The new cultivar of shrub rose can be readily distinguished from its parents and other cultivars. The female parent, 'MACrexy', is a florabunda and has flowers that are pink in color and slightly fragrant. The male component of the male parent, 'MEIpotal', has carmine pink flowers with a white eye that are comprised of 5 petals that lack fragrance. The cultivars 'MEIcoublan' (U.S. Plant Pat. No. 6,088) and 'Sea Foam' (U.S. Plant Pat. No. 2,463) are the closest comparison roses. They both have similarity to 'BAIrift' in that they are shrub roses having fully white double flowers. The differ from 'BAIRift' in that 'MEIcoublan' is shorter in height, has a spreading growth habit and is everblooming while 'Sea Foam' has double flowers that are not as full, white and yellow flower buds, and a compact rounded plant habit.

BRIEF DESCRIPTION OF THE DRAWING

The accompanying colored photographs illustrate the overall appearance and distinct characteristics of the new shrub rose, 'BAIrift', as grown outdoors in trail blocks and containers in St. Paul, Minn. and Yamhill, Oreg. The photographs were taken of two to three year-old plants grown on their own roots.

Figure 1:
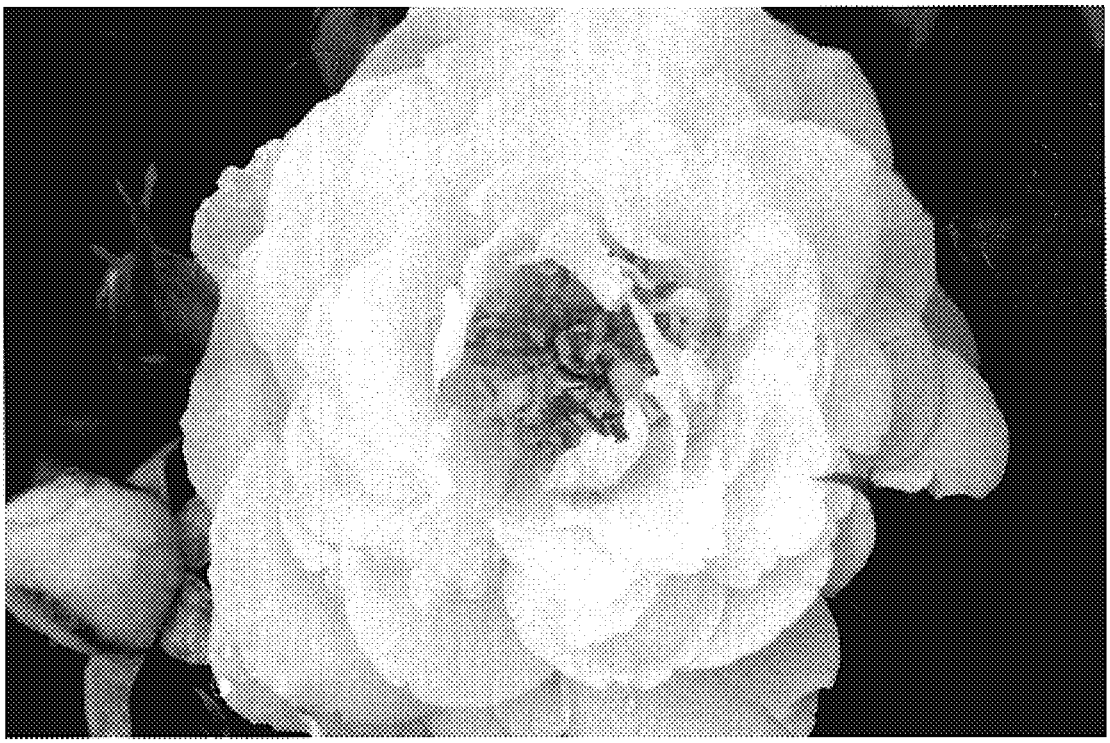
FIG. 1 provides a view of a fully open flower with developing flower buds.
Figure 2:
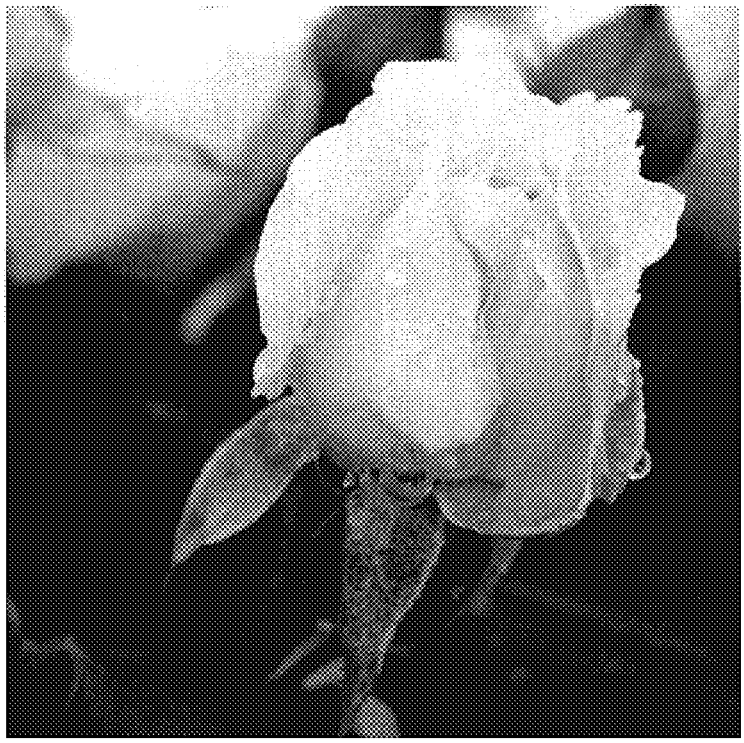
FIG. 2 provides a view of a flower bud just prior to opening.
Figure 3:
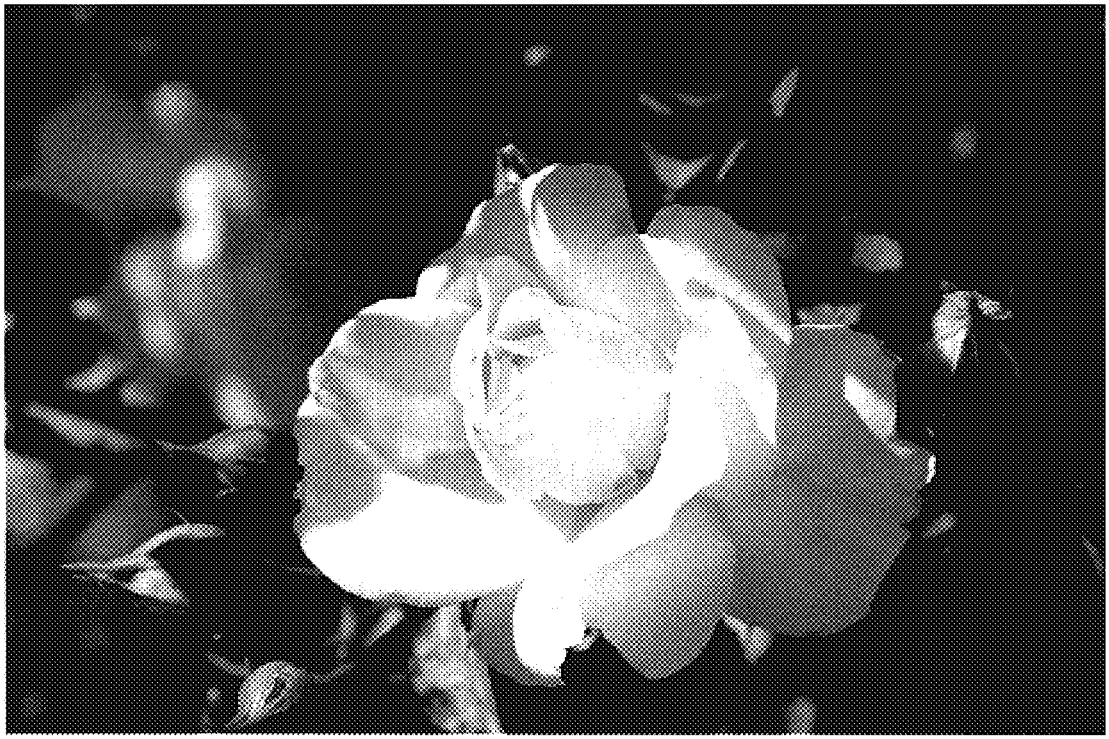
FIG. 3 provides a view of an opening flower with flower buds at various stages of development.
Figure 4:
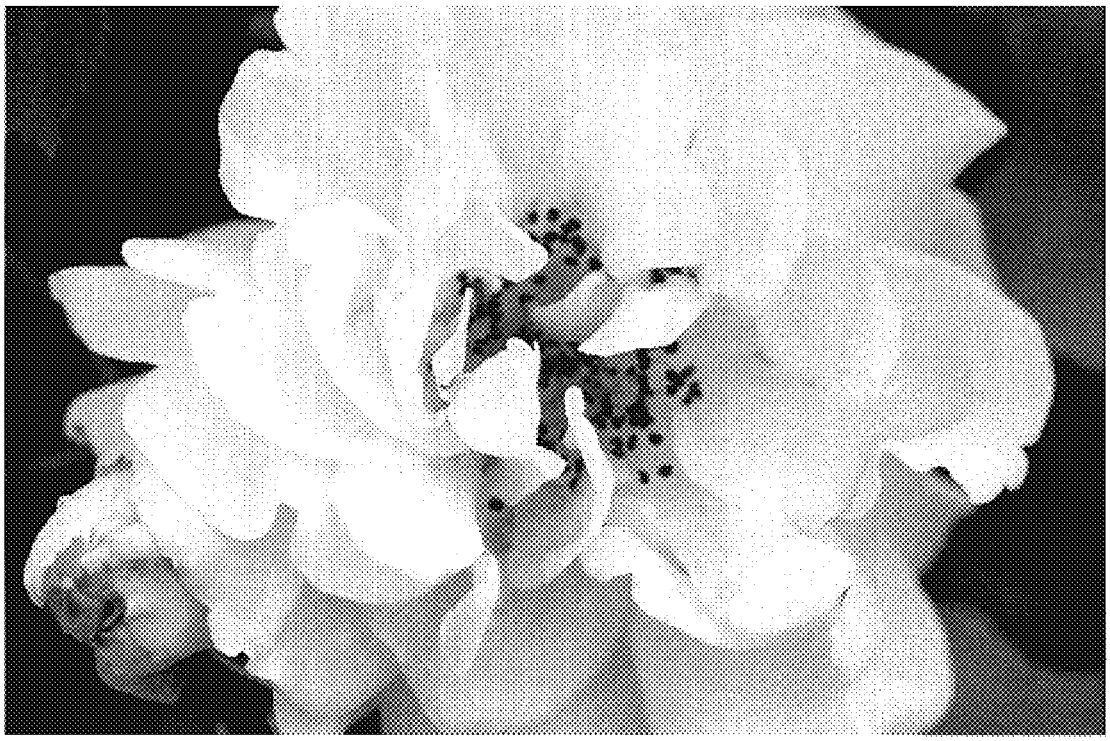
FIG. 4 provides a view of a mature flower.

The colors in the photographs are as close as possible with digital photography techniques available, the color values cited in the detailed botanical description accurately describe the colors of the new shrub rose.

DETAILED BOTANICAL DESCRIPTION

The following is a detailed description of the new cultivar as observed on two year-old container plants and three year-old field-grown plants as grown outdoors in Yamhill, Oreg. and St. Paul, Minn. The phenotype of the new cultivar may vary with variations in environmental, climatic, and cultural conditions, as it has not been tested under all possible environmental conditions. The color determination is in accordance with the R.H.S. Colour Chart of The Royal Horticultural Society, London, England, except where general color terms of ordinary dictionary significance are used.

General description:

*Botanical classification.*—*Rosa hybrida* 'BAIrift'.

*Parentage.*—Seed parent *Rosa* 'MACrexy', pollen parent *Rosa* 'MEIpotal'.

*Blooming habit.*—Abundant in May and June and recurrent throughout the growing season.

*Plant habit.*—Upright and arching, uniform.

*Height and spread.*—90 to 125 cm in height and 80 to 100 cm in spread.

*Cold hardiness.*—U.S.D.A. Zone 4 to 9.

*Diseases and pests.*—High degree of resistance observed to rose blackspot (*Diplocarpon rosae*) and powdery mildew (*Sphaerotheca pannosa* var. *rosa*).

*Propagation.*—Softwood stem cuttings, own roots.

*Growth.*—Vigorous and strong.

Branch Description:

*Stem color.*—Young; 144A, maturing; 138A, mature wood; 197A with areas of 138B showing through.

*Stem surface.*—Young and mature; glabrous and glaucous, adult wood; mostly glabrous with bark-like ridges.

*Stem size.*—Average of 3 mm in width (range 2 to 7 mm) and up to 30 cm in height.

*Thorns.*—Narrowly triangular in shape and horizontal to slightly curved downward, oval base, average of 5 per 5 cm in number, average of 5 mm in length with a base 5 mm in length and 2 mm in width, color 138A suffused with 183B and a base 138A.

Foliage Description:

*Leaves.*—Division is odd-pinnate, arrangement is alternate, average of 6.5 cm in length and 4.5 cm in width, internode length is an average of 1.7 cm.

*Leaflets.*—Typically 7 (3 or 5 less common), broadly oval in shape, rounded to cuneate base, acute to cuspidate apex, finely serrated margins, glabrous and dull on upper surface and finely pubescent on lower surface, average of 2.5 cm in length and 2 cm in width, color: young leaves upper and lower surface; 137D, mature leaves upper surface; 137A, mature leaves lower surface; 138A.

*Rachis.*—Average of 4.75 cm in length and 1.2 mm in diameter, color of upper surface 138A, color of lower surface 144A, surface is glabrous with small thorns on underside (about 3 per rachis).

*Stipules.*—Parallel with auricle facing outward, average of 1 cm in length and 4 mm in width, color on upper side is 144 apex of 137A and 144C on middle ridge, color of lower surface is 144A with apex of 137A.

*Petioles.*—Average of 8 mm in length and 1.2 mm in diameter, color of upper surface 138A, color of lower surface 144A, glabrous surface.

Inflorescence Description:

*Inflorescence type.*—Fully double flowers arranged in corymbs.

*Flower number.*—Average of 3 per lateral stem, about 20 per 2 gallon plant.

*Flower fragrance.*—Strong rose scent.

*Flower longevity.*—About 3 to 5 days, depending on temperature and sunlight exposure.

*Flower type.*—Very fully double.

*Flower size.*—Average of 5 cm in diameter and 3.2 cm in depth.

*Peduncles.*—Stiff, average of 4.5 cm in length and 2 mm in diameter, sparsely pubescent, color is 138A, color is 145C in shaded side.

*Bracts.*—Average of 3 per flower, range from 1 to 3 cm in length and 3 to 6 mm in width, lanceolate to linear in shape, serrated margins, acuminate to leaf-like apex, and cuneate base, sessile, upper surface 137A in color, lower surface 146A in color.

*Flower buds.*—Ovate in shape, medium in size with an average of 1.8 cm in length and 1.6 cm in width prior to opening, color 155B with edges of petals marked with 71C to 71D.

*Sepals.*—5, broadly lanceolate in shape, margin is entire and tomentose, color of upper surface 191A, color of lower surface 138A, upper surface is canascent with white tint due to short white hairs, lower surface is finely pubescent but satiny, average of 1.8 cm in length and 6 mm in width, apex is apiculate changing to a small leaf, base is truncate, aspect is upright in tight bud stage changing to reflexed when bud opens.

*Petals.*—About 50, drop readily and cleanly, orbicular to obovate in shape and curled on the apex and sides, upper and lower surface is glabrous and satiny, entire margin, cuneate base, apex is typically rounded but occasionally slightly cuspidate or cordate, average of 2.5 cm in length and 2.5 cm in width, color: opening flowers upper and lower surface; 155D, fully open flowers upper and lower surface; 155D, base petal spot; none.

*Receptacle.*—Average of 6 mm in diameter and 6 cm in depth when flower is fully open, funnel shaped, glabrous and satiny, 144A in color with 144B.

*Pistils.*—About 20, stigma is an average of 0.5 mm in length, an average of 1 mm in width and 2A in color, style is an average of 7 mm in length and 145C in color towards the base and 63A in color towards apex.

*Stamens.*—About 60, appear deformed, filaments are about 1.1 cm in length and 155A in color, anthers are an average of 3.2 mm in length, an average of 1.3 mm in width and 199B in color, pollen is 11B in color.

*Hips.*—Round in shape and yellow-orange in color.

I claim:

1. A new and distinct cultivar of shrub rose plant named 'BAIrift' as herein illustrated and described.

* * * * *

UNITED STATES PATENT AND TRADEMARK OFFICE

CERTIFICATE OF CORRECTION

PATENT NO. : PP 19,036 P2
APPLICATION NO. : 11/809230
DATED : July 15, 2008
INVENTOR(S) : Lim It is certified that error appears in the above-identified patent and that said Letters Patent is hereby corrected as shown below:

On title page

Please delete the following:

Item "(50) Latin Name: Rosa hybrida
Varietal Denomination: BAIrefit"

Please insert the following :

Item --(50) Latin Name: Rosa hybrida
Varietal Denomination: BAIrift--

Signed and Sealed this

Twelfth Day of January, 2010

David J. Kappos

David J. Kappos
*Director of the United States Patent and Trademark Office*